United States Patent
Jerry (10) Patent No.: US 9,675,464 B2
(45) Date of Patent: Jun. 13, 2017

(54) TIBIAL TRAY SYSTEM AND METHOD OF IMPLANTATION

(76) Inventor: Gerald J. Jerry, Port Huron, MI (US)

( * ) Notice: Subject to any disclaimer, the term of this patent is extended or adjusted under 35 U.S.C. 154(b) by 140 days.

(21) Appl. No.: 13/881,606

(22) PCT Filed: Oct. 28, 2011

(86) PCT No.: PCT/US2011/058324
§ 371 (c)(1),
(2), (4) Date: Apr. 25, 2013

(87) PCT Pub. No.: WO2012/058560
PCT Pub. Date: May 3, 2012

(65) Prior Publication Data
US 2013/0226304 A1    Aug. 29, 2013

Related U.S. Application Data (60) Provisional application No. 61/407,691, filed on Oct. 28, 2010, provisional application No. 61/407,836, filed on Oct. 28, 2010.

(51) Int. Cl.
*A61F 2/38* (2006.01)
*A61F 2/30* (2006.01)

(52) U.S. Cl.
CPC ............ *A61F 2/389* (2013.01); *A61F 2/3868* (2013.01); *A61F 2/3859* (2013.01)

(58) Field of Classification Search
CPC ................................. A61F 2/389; A61F 2/461
USPC .......................................... 623/20.14–20.29
See application file for complete search history.

(56) References Cited

U.S. PATENT DOCUMENTS

| | | | |
|---|---|---|---|
| 3,765,033 A * | 10/1973 | Goldberg et al. | 623/20.26 |
| 3,774,244 A | 11/1973 | Walker | |
| 4,586,933 A | 5/1986 | Shoji et al. | |
| 4,888,021 A * | 12/1989 | Forte et al. | 623/20.19 |
| 5,080,675 A | 1/1992 | Lawes et al. | |
| 5,395,401 A * | 3/1995 | Bahler | 623/20.29 |
| 6,080,195 A * | 6/2000 | Colleran | A61F 2/3886 |
| | | | 623/20.32 |
| 6,946,001 B2 | 9/2005 | Sanford et al. | |
| 7,081,137 B1 | 7/2006 | Servidio | |
| 2003/0171811 A1* | 9/2003 | Steiner | A61L 27/386 |
| | | | 623/13.17 |
| 2004/0102852 A1 | 5/2004 | Johnson et al. | |
| 2004/0162620 A1 | 8/2004 | Wyss | |
| 2004/0193280 A1 | 9/2004 | Webster et al. | |
| 2005/0070906 A1 | 3/2005 | Clark et al. | |
| 2005/0187635 A1 | 8/2005 | Metzger | |
| 2006/0004460 A1 | 1/2006 | Engh et al. | |
| 2007/0173858 A1* | 7/2007 | Engh et al. | 606/99 |
| 2008/0091272 A1* | 4/2008 | Aram et al. | 623/20.34 |
| 2008/0119938 A1 | 5/2008 | Oh | |

(Continued)

*Primary Examiner* — Ann Schillinger
(74) *Attorney, Agent, or Firm* — Brooks Kushman P.C.

(57) ABSTRACT

A tibial tray system includes a tibial tray configured for attachment to a surgically-prepared surface of the proximal end of the tibia. The tibial tray includes a track disposed in a generally A-P direction. The tibial tray system also includes a spline configured to engage the track and to be positionable in at least one location along the track. The spline includes a bearing surface that is configured to contact a femoral component of the knee prosthesis to guide movement of the femoral component during extension and flexion of the knee.

20 Claims, 6 Drawing Sheets

(56) References Cited

U.S. PATENT DOCUMENTS

| | | | |
|---|---|---|---|
| 2008/0167722 A1* | 7/2008 | Metzger | A61F 2/30721 623/20.36 |
| 2008/0243260 A1* | 10/2008 | Lee et al. | 623/20.33 |
| 2008/0243261 A1 | 10/2008 | Wyss et al. | |
| 2008/0243263 A1 | 10/2008 | Lee et al. | |
| 2009/0204222 A1 | 8/2009 | Burstein et al. | |
| 2009/0264894 A1* | 10/2009 | Wasielewski | A61F 2/38 606/102 |
| 2009/0306784 A1* | 12/2009 | Blum | A61B 17/1714 623/20.21 |
| 2009/0306786 A1 | 12/2009 | Samuelson | |
| 2010/0234961 A1 | 9/2010 | Otto et al. | |
| 2013/0245777 A1 | 9/2013 | Jerry | |

\* cited by examiner

TIBIAL TRAY SYSTEM AND METHOD OF IMPLANTATION

CROSS-REFERENCE TO RELATED APPLICATIONS

This application claims the benefit of U.S. provisional patent application Nos. 61/407,691 and 61/407,836 each filed 28 Oct. 2010, and each of which is hereby incorporated herein by reference.

TECHNICAL FIELD

The present invention relates to a surgically implantable tibial tray system and a method for implanting such a system.

BACKGROUND

Despite the advancements in implant design and surgical technique, total knee replacements still have certain limitations, and postoperative results can be less than desired. One issue that may arise is pain associated with movement of the knee, especially at deep flexion. There can be any number of causes for this, including inflammation of the soft tissue in and around the knee area. The inflammation may be caused by impingement of the tissue by the implant as it articulates, particularly when it articulates at the extremes of its range, such as during deep flexion. Therefore, it would be desirable to provide a knee replacement system that overcomes the problems described above, particularly with regard to the tibial components, and allows a more anatomic range of motion for the patient without the pain associated with movements such as deep flexion.

SUMMARY

Embodiments of the invention overcome at least some of the problems described above and provide a greater range of motion without the pain associated with some implant designs.

Embodiments of the invention include a modular tibial tray system that may include separate medial and lateral tibial inserts, a tibial tray, and an intramedullary stem.

Embodiments of the invention also include a tibial tray system for a knee, which has a tibial tray configured for attachment to a surgically-prepared surface of a proximal end of a tibia. The tibial tray may include a track disposed in a generally anterior-posterior (A-P) direction. The tibial tray system also includes a spline configured to engage the track and to be positionable in at least one location along the track. The spline includes a bearing surface configured to contact a femoral component of a knee prosthesis to guide movement of the femoral component during extension and flexion of the knee.

Embodiments of the invention further include a tibial tray system for a knee, having a tibial tray configured for attachment to a surgically-prepared surface of a proximal end of a tibia, and including a platform and a keel extending outward from the platform for insertion into the tibia. The platform includes an aperture disposed therethrough positioned to facilitate reattachment of an anterior cruciate ligament through the aperture, the aperture being closed to at least a posterior edge of the tibial tray.

Embodiments of the invention also include a tibial tray system for a knee, with a tibial tray configured for attachment to a surgically-prepared surface of a proximal end of a tibia. The tibial tray includes a platform having an attachment feature, and a keel extending outward from the platform for insertion into the tibia. The tibial tray system also includes a spline configured to mate with the attachment feature to secure the spline to the attachment feature, the spline including a bearing surface configured to contact a femoral component of a knee prosthesis to guide movement of the femoral component during extension and flexion of the knee.

Embodiments of the invention further include a method for implanting a tibial tray system in a knee. The tibial tray system includes a tibial tray having an aperture therein. The method includes: preparing graft material for an ACL, stabilizing the graft material on a femoral portion of the knee, passing the graft material through an anterior opening in the tibial tray, and attaching the graft material to the tibia.

DETAILED DESCRIPTION

Figure 1:
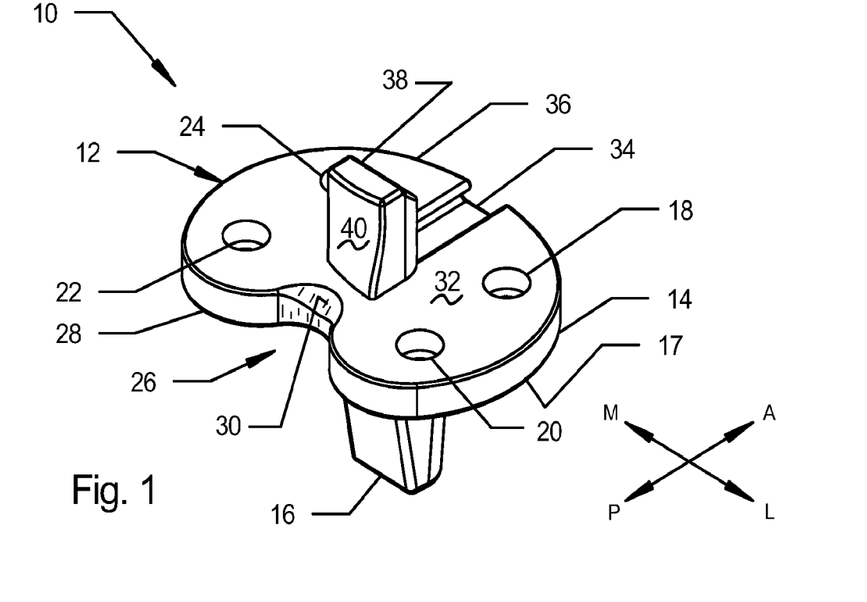
FIG. 1 shows a tibial tray system in accordance with embodiments of the present invention.

FIG. 1 shows a tibial tray system 10 in accordance with embodiments of the present invention. The tibial tray system 10 includes a tibial tray 12 configured for attachment to a surgically-prepared surface of a proximal end of a tibia. The tibial tray 12 is configured for a right knee, with the medial-lateral (M-L) and anterior-posterior (A-P) directions being indicated by the arrows shown in FIG. 1. The tibial tray 12 includes a platform 14 and a keel 16 extending outward from a distal surface 17 of the platform 14 for insertion into the tibia. A number of screw holes 18, 20, 22, 24 are disposed through the platform 14 to allow the tray 12 to be secured to a patient's tibia. Screws may be used in conjunction with, or replaced by, bone cement or other type of fixation mechanism.

The tibial tray 12 includes a notch 26 disposed along a posterior edge 28. The notch 26 includes a chamfer 30 that provides a smooth transition from a proximal surface 32 of the tray 12 to the posterior edge 28. This helps to avoid impingement and possible inflammation of a posterior cruciate ligament (PCL), which can be retained using the tibial tray system 10 shown in FIG. 1. The tibial tray 12 includes an attachment feature, which in the embodiment shown in FIG. 1, is a track 34. Shown in FIG. 1, the track 34 is disposed in a generally A-P direction, and is open to an anterior edge 36 of the tray 12, and is closed to the posterior edge 28.

The tibial tray system 10 also includes a spline 38 that is configured to mate with the attachment feature, which in this embodiment means that the spline 38 is configured to engage the track 34. When the spline 38 engages the track 34, the mechanism of which is described in more detail below, the spline 38 is positionable at any of a number of locations along the track 34. Other types of attachment features are contemplated for a tibial tray system in accordance with embodiments of the invention. For example, a number of recesses can be machined in a platform of a tibial tray along an A-P axis such that a spline could be located at a number of discrete locations. Alternatively, a single aperture can be disposed in a platform of a tibial tray, and any one of several different splines having a mating plug chosen to cooperate with the aperture—see below with regard to FIGS. 4A and 4B. In the embodiment shown in FIG. 1, the spline 38 is held in position by an interference fit between the spline 38 and the track 34.

Figure 2:
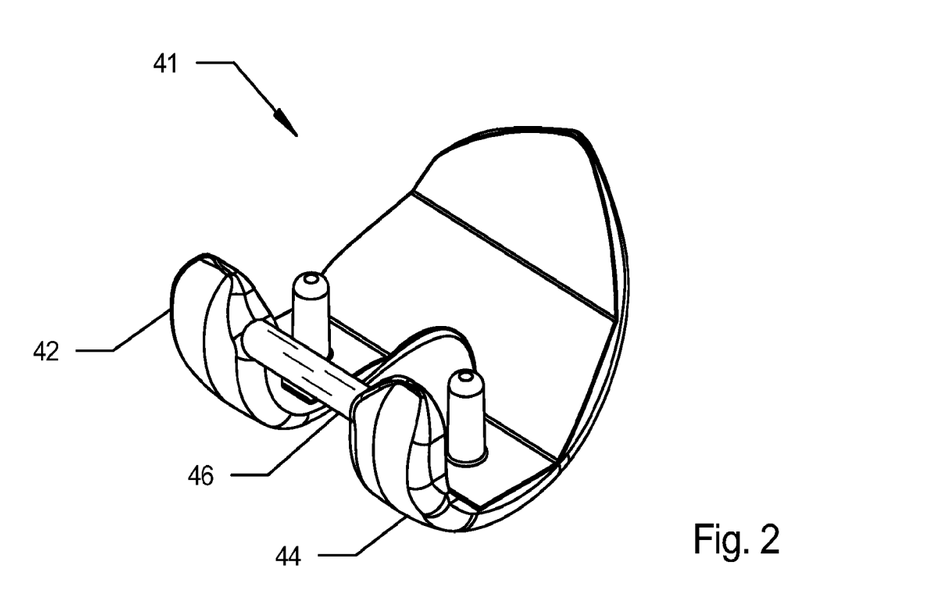
FIG. 2 shows a femoral component of a knee prosthesis for use with a tibial tray system in accordance with embodiments of the invention.

The spline 38 includes a bearing surface 40 configured to contact a femoral component of the knee prosthesis to guide movement of the femoral component during extension and flexion of the knee. Such a femoral component 41 is illustrated in FIG. 2, where the medial condyle 42 is connected to the lateral condyle 44 by an intercondylar post 46. As explained more fully below, the post 46 is configured to interface with the bearing surface 40 of the spline 38 so that the femoral component 41 moves with a motion during extension and flexion that closely resembles anatomic motion of a healthy knee. The femoral component 41 shown in FIG. 2 is oriented in the same directions as the tibial tray system 10 shown in FIG. 1. When viewed in a coronal plane—i.e., in a generally A-P direction—the lateral condyle 44 of the femoral component 41 is narrower than the medial condyle 42. This feature helps to reduce impingement as the knee is moved into deep flexion.

Figure 3A:
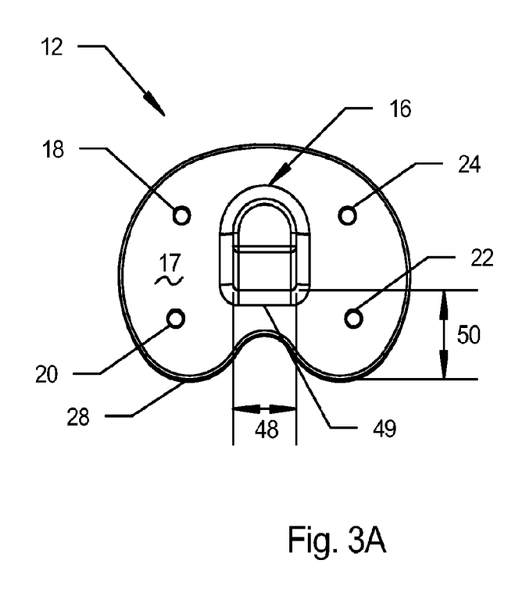
FIG. 3A shows a bottom plan view of a tibial tray in accordance with embodiments of the invention.
Figure 3B:
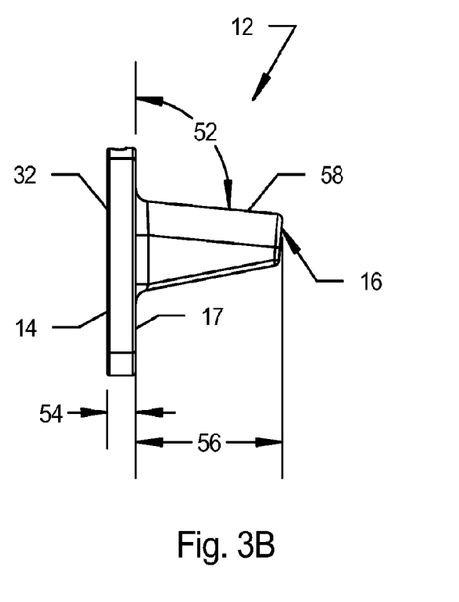
FIG. 3B shows a side view of the tibial tray shown in FIG. 3A.

FIG. 3A shows a bottom of the tibial tray 12, and in particular, the distal surface 17. The keel 16 as a width 48 of approximately 0.6 inches (in.) in the embodiment shown in FIG. 3A, and it has a proximal edge 49 disposed at a distance 50 of approximately 0.75 in. from the posterior edge 28 of the tray 12. The dimensions given herein are indicative of one size of the embodiment of the tibial tray shown in FIG. 3A. Other embodiments of the present invention will have different dimensions as the tray is scaled up or down in size; moreover, the dimensions 48, 50 may not be exactly scaled for different sizes of trays. The same is true for dimensions 52, 54, 56 shown in FIG. 3B. In the illustrated embodiment, the keel 16 forms an angle 52 of approximately 95° from the distal surface 17 to an anterior edge 58. The platform 14 has a thickness 54 of approximately 7 mm, and the keel 16 extends outward from the distal surface 17 approximately 37 mm.

Figure 4A:
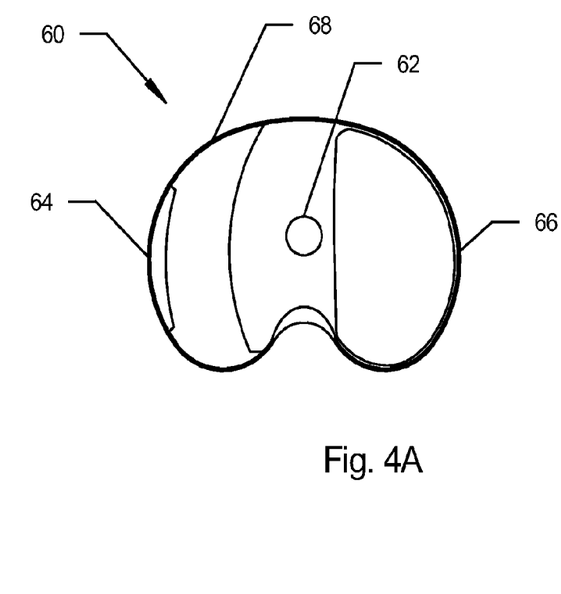
FIG. 4A shows a top plan view of a tibial tray configured for separate tibial inserts in accordance with embodiments of the invention.

FIG. 4A shows a tibial tray 60 in accordance with embodiments of the present invention. Like the tibial tray 12, shown in FIG. 1, the tibial tray 60 includes an attachment feature; however, on the tibial tray 60, the attachment feature is in the form of a tapered hole 62 rather than a track. As discussed below in conjunction with FIG. 4B, the hole 62 is configured to receive a portion of a spline, such as the spline 38 shown in FIG. 1. As illustrated in FIG. 1, the tibial tray 12 can receive a tibial insert system which includes a tibial insert or inserts along the proximal surface 32, to be attached by any of a number of known methods of attachment—e.g., snap fit, dovetail, etc. Moreover, the tray 12 can be used with a single tibial insert having medial and lateral sides, or with separate medial and lateral inserts. In contrast, the tibial tray 16 shown in FIG. 4A is specifically configured to receive a tibial insert system having two separate tibial inserts, one on the medial side 64 and another on the lateral side 66.

As shown in FIG. 4A, the medial side 64 of the tibial tray 60 is configured with an arcuate track 68 that is disposed generally in an A-P direction. As described in more detail in FIG. 5, the arcuate track 68 is configured to facilitate movement of a movable medial insert as a femoral component, such as the femoral component 41 shown in FIG. 2, moves relative to the tibial tray 60 during extension and flexion of the knee. The track 68 may be configured as a keyway with a dovetail geometry similar to the track 34 (see FIG. 1), which is configured to receive and allow movement of a spline, such as the spline 38 shown in FIG. 1. In contrast to the medial side 64 of the tray 60, the lateral side 66 is configured to receive a tibial insert that will be fixed in the tray 60. Such an insert may be secured to the tray 60 via a snap fit or some other known mechanism.

Figure 4B:
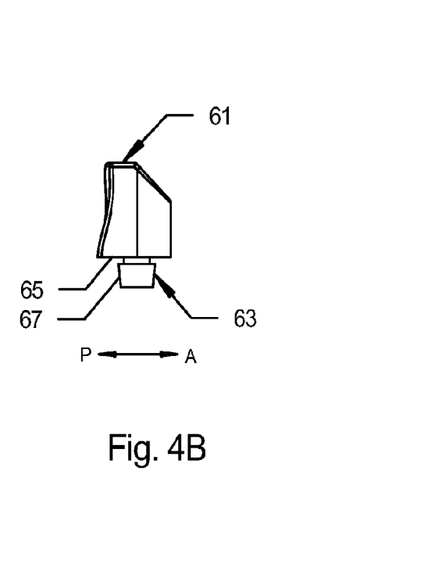
FIG. 4B shows a side view of a spline configured for use with the tibial tray shown in FIG. 4A.

FIG. 4B shows a spline 61 configured to mate with the tibial tray 60, and in particular, the spline 61 includes a projection 63 extending outward from a distal side 65. The projection 63 is configured as a tapered shank 67 configured to be secured in the aperture 62 in the tibial tray 60. The shank 67 and the aperture 62 may each have a Morse or other type of taper to ensure secure mating between the parts. As an alternative to the round aperture 62 and shank 67 illustrated in the drawing figures, a square or rectangular aperture and shank could also be employed. The shank 67 may be located at any of a variety of A-P locations along the distal side 65 of the spline 61. This permits a surgeon to choose a shank location that provides the best A-P fit for the spline 61 when it is mated with the tibial tray 60. Although the tapered hole/shank attachment features are illustrated here in conjunction with a tibial tray having separate movable and fixed tibial inserts, this shank attachment mechanism can be used with other embodiments of the tibial tray system of the present invention.

Figure 5A:
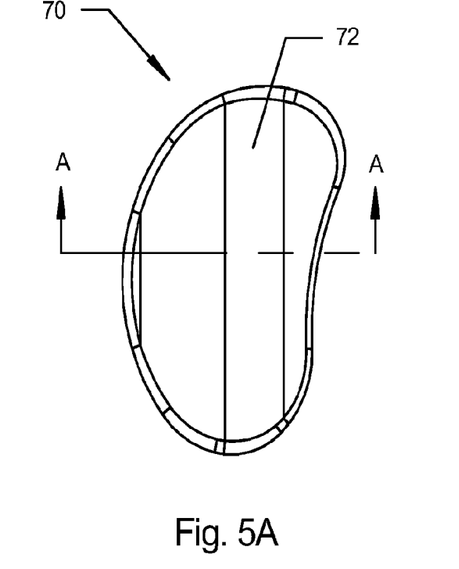
FIGS. 5A and 5B show different views of a movable medial tibial insert in accordance with embodiments of the invention.
Figure 5B:
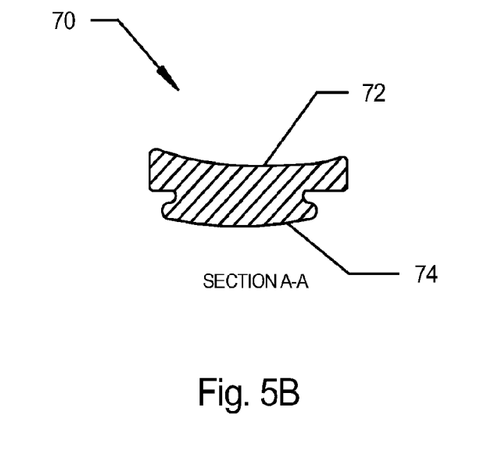
Figure 6:
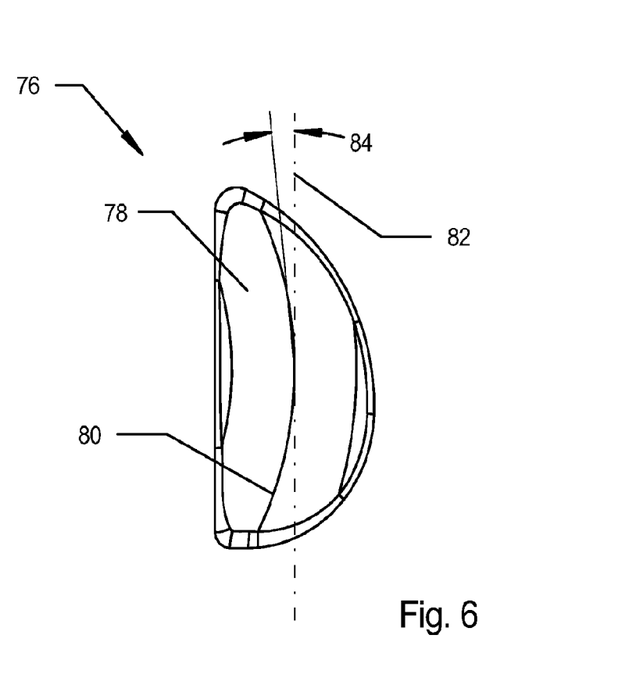
FIG. 6 shows a top plan view of a fixed lateral tibial insert in accordance with embodiments of the invention.

FIG. 5A shows a medial insert 70 for use with the tibial tray 60 shown in FIG. 4A. The insert 70 has an articulating surface 72 that is generally straight in an A-P direction. FIG. 5B shows a sectional view of the insert 70 taken through section lines A-A shown in FIG. 5A. As shown in FIG. 5B, the insert 70 includes a key 74 configured to translate within the keyway 68 of the tray 60 shown in FIG. 4A. Conversely, a lateral tibial insert 76 shown in FIG. 6, is configured for fixed attachment on the lateral side 66 of the tray 60. The lateral insert 76 includes an articular surface 78, which, like the articular surface 72 of the medial insert 70, is configured to act as a bearing surface and to articulate relative to an articular surface of a femoral component, such as the femoral component 41 shown in FIG. 2.

As shown in FIG. 6, the articular surface 78 is generally arcuate, forming a curve 80 that moves medially at the A-P extremes, and moves laterally near the center of the insert 76. An A-P axis 82 shows that the arcuate curve 80 of the articular surface 78 is not symmetric; rather, it is offset by an angle 84. In the embodiment shown in FIG. 6, the angle 84 is approximately 2.5°; however, an angle between 2°-4° may be used or even an angle between 1°-10°. Other angles, or indeed no offset angle, may be used depending on the desired geometric configuration.

Similarly, the arcuate track 68 on the tibial tray 60 shown in FIG. 4A may have an offset angle like the offset angle 84 of the articular surface 78. A patient may have a tibia that articulates along an offset arcuate path, with different patients having arcuate articulating paths offset by different angles. Indeed, the same patient may have different offset angles for each knee, and even different angles on the different sides of the same knee. To facilitate a fit that is as close to anatomic as possible, radiographic information, for example, from a CT scan or MRI, can be used to choose a tray and insert combination having the right offset angles for each patient. A detailed description of a tibial arrangement having one fixed and one mobile tibial insert is described in international patent application no. PCT/US11/58291, entitled "Knee System", filed on 28 Oct. 2011, and which is incorporated herein by reference.

Figure 7A:
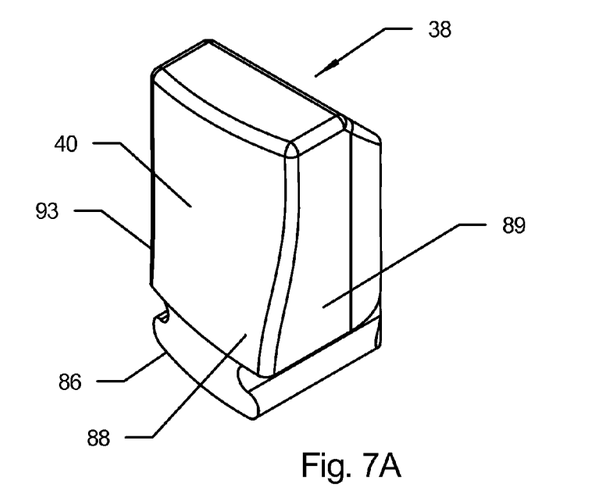
FIG. 7A-7C shows an different views of a spline for use with a tibial tray in accordance with embodiments of the invention.

FIG. 7A shows the spline 38 (see also FIG. 1) in a perspective view illustrating the bearing surface 40 and a tracking feature 86 configured to cooperate with the track 34 in the tibial tray 12, shown in FIG. 1. The tracking feature 86 is configured as a key having a dovetail geometry that allows it to be positioned anywhere along the track 34. This is a similar configuration to the key 74 on the medial tibial insert 70 shown in FIGS. 5A and 5B. Also shown in FIG. 7A is a projection 88 of the bearing surface 40 disposed toward a lateral side 89 of the spline 38. The projection 88 is also disposed distally on the spline 38, and may be referred to as a distal lateral eminence. It is configured to contact a portion of a femoral component, for example, the post 46 on the femoral component 41 shown in FIG. 2. The projection 88 is configured to guide at least a portion of the femoral component 41 posteriorly relative to the tibial tray during flexion of the knee. This is described in more detail below in conjunction with FIG. 7C.

Figure 7B:
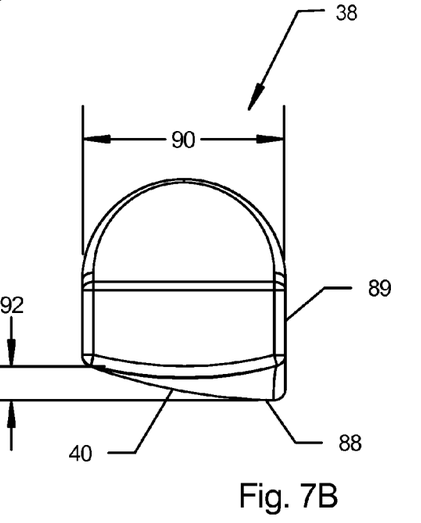

FIG. 7B shows a top view of the spline 38, and illustrates a width dimension 90, which in this embodiment is approximately 14 mm. Also in the embodiment shown in FIG. 7B, the projection 88 is disposed outward from a medial side of the bearing surface 40 by a distance 92 of approximately 2.5 mm. As noted above with the other dimensions, different embodiments may have different dimensions, as it is contemplated that embodiments of the present invention will be suitable for many different patients' knee geometries and sizes.

Figure 7C:
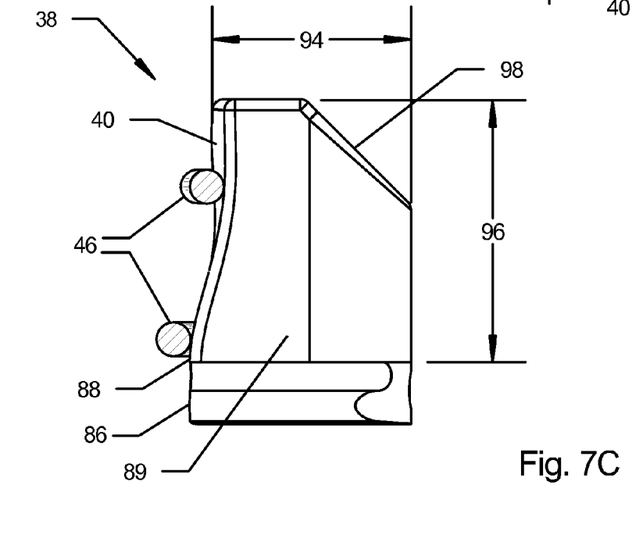

As shown in FIG. 7C, when the post 46 contacts the distal lateral eminence 88, the portion of the post 46 near the lateral side 89 of the spline 38 is moved posteriorly. Because the projection 88 extends outward from other portions of the bearing surface 40, a portion of the post 46 near a medial side 93 (see FIG. 7A) of the spline 38 is anteriorly displaced relative to the post 46 near the lateral side 89. In essence, this causes a slight rotation of the post 46, and therefore the femoral component 41 to which it is attached, as the knee flexes and the post 46 moves downward along the bearing surface 40. Thus, as the knee flexes, a right knee will rotate slightly in a clockwise direction as viewed from the top, while a left knee will rotate slightly in a counterclockwise direction.

Conversely, when the post 46 is more proximally disposed on the bearing surface 40 (higher up on the view of the spline 38 shown in FIG. 7C), which may be approximately ⅔ of the height of the spline 38, the post 46 and therefore the femoral component 41, are slightly rotated in the opposite direction. This very closely mimics the movement of a healthy anatomical knee, and provides a mechanism for deep flexion without impingement of soft tissue and its associated pain. Also shown in FIG. 7C is that the spline 38 has a thickness 94 of approximately 13.5 mm, and a height 96 of approximately 18 mm. In the embodiment shown in FIG. 7C, the spline 38 also includes a reduced edge 98 disposed toward an anterior portion of the spline 38. The reduced edge 98 also reduces helps to inhibit interference between the spline 38 and the femoral component 41 during extension and flexion of the knee.

In addition to facilitating anatomical movement of the knee during extension and flexion, embodiments of the present invention also help to maintain normal anatomic geometry of the bones relative to each other. For example, the tibial tray system 10 described above can be implanted, and the spline 38 adjusted, such that the distance between the proximal edge of a tibia and femur is 8-15 mm at 90° flexion, which is what is expected during normal flexion of the knee.

As noted above, the tray 12 shown in FIG. 1, and even the tray 60 shown in FIG. 4A, provide a posterior notch to allow a PCL to be retained during surgery. Each of these trays 12, 60, however, are considered to be cruciate sacrificing trays with regard to the anterior cruciate ligament (ACL). In contrast, tibial tray system 100 shown in FIG. 8A includes a tibial tray 102 which facilitates retention of both the ACL and PCL. The tibial tray 102 is configured for attachment to a surgically-prepared surface of a proximal end of a tibia, and includes a platform 104 and a keel 106 extending outward from the platform 104 for insertion into the tibia. The platform 104 includes an intercondylar notch 108 similar to the notch 30 shown in the tray 12 in FIG. 1. The platform 104, however, has an additional feature in the form of an aperture 110 disposed in a generally anterior position through the platform 104. The aperture 110 is closed to both an anterior edge 109 and a posterior edge 111 of the tray 102. It is contemplated that an aperture, such as the aperture 110, will be closed to at least a posterior edge of the tray—i.e., such an aperture will not form a part of a posterior notch of the type used for bi-cruciate tibial tray designs.

The aperture 110 is sized and positioned to facilitate reattachment of ACL through the aperture, for example, via and allograft or autograft procedure. In order to facilitate such procedures, the aperture 110 is oriented through the platform 104 by a compound angle. Specifically, the aperture 110 is disposed at an angle 112 of approximately 25.5° from an A-P axis 114 as viewed in a top plan view. The second of the two angles 116 is illustrated in FIG. 8B, and a center line 117 of the aperture 110 is approximately 40° from a proximal-distal axis 118. In the embodiment illustrated in FIGS. 8A and 8B, the aperture 110 has a diameter 120 of approximately 12 mm, and goes through a portion 122 of the keel 106. It is worth noting that the tibial tray 102 is a right tray, and a tray configured for a left knee would require different geometry.

The specific size and angle of an ACL retaining aperture, such as the aperture 110, may vary depending on the size of the tibial tray, the geometry of the patient's knee, as well as the particular surgical procedure being used. To allow even greater flexibility in positioning the tibial tray to facilitate the ACL reattachment procedure, embodiments of the present invention may include an intramedullary rod that attaches to a keel, such as the keel 106. Such a keel can be configured with a Morse taper hole to receive a Morse taper stem on the end of the intramedullary rod. The Morse taper hole and the Morse taper rod can both be configured to be off center such that rotation of the intramedullary rod relative to the tibial tray allows the tibial tray to be positioned at the most favorable location for the ACL reattachment.

Figure 8A:
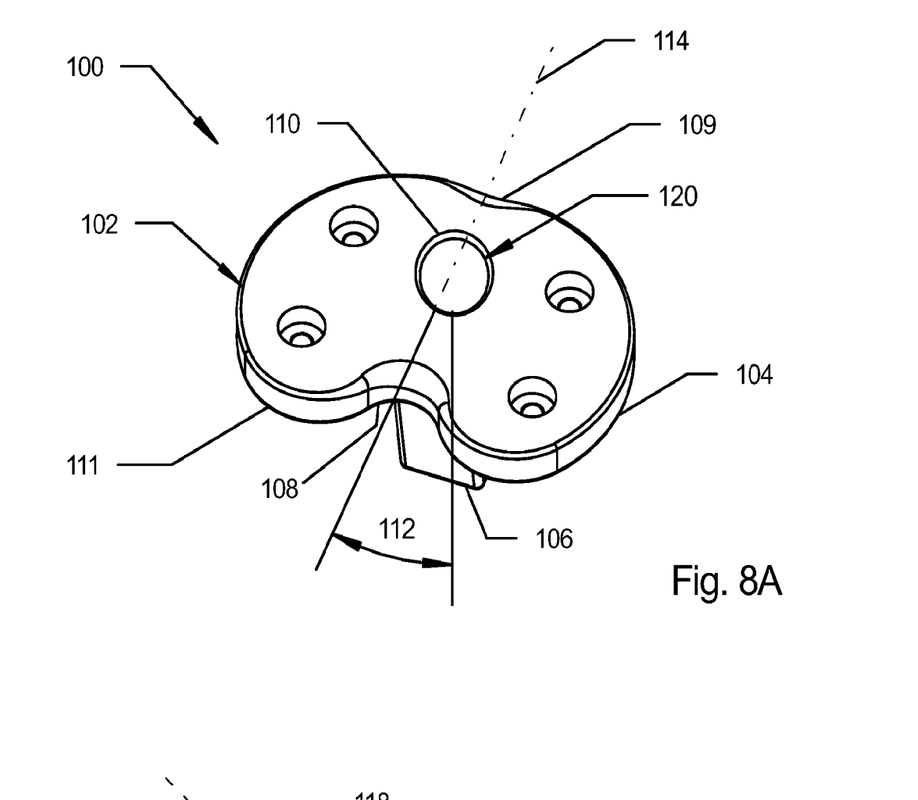
FIGS. 8A and 8B show different views of a tibial tray in accordance with embodiments of the invention.
Figure 8B:
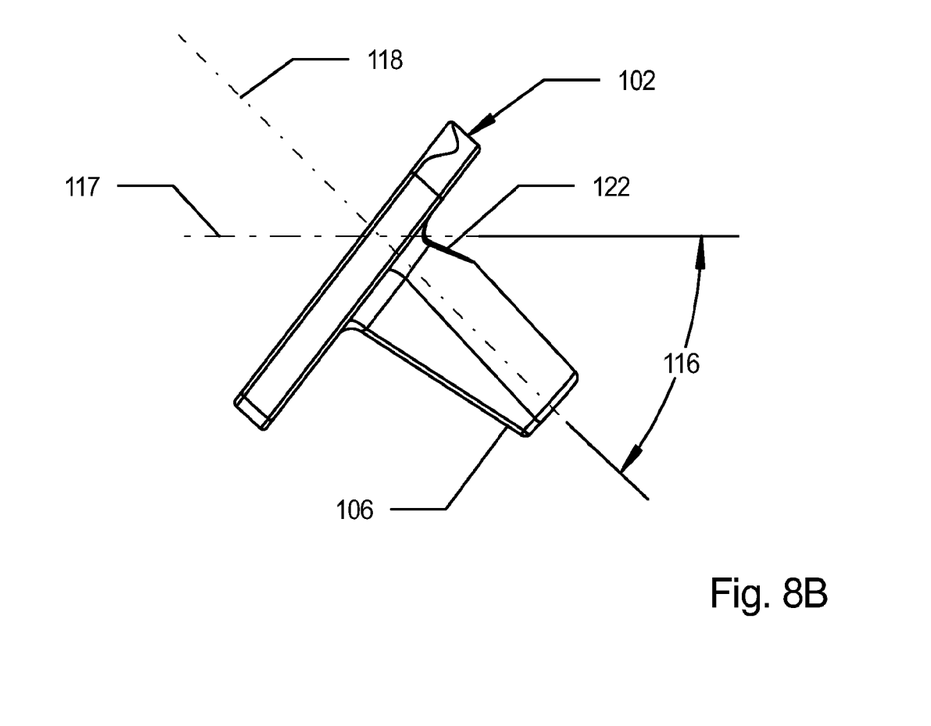
Figure 9:
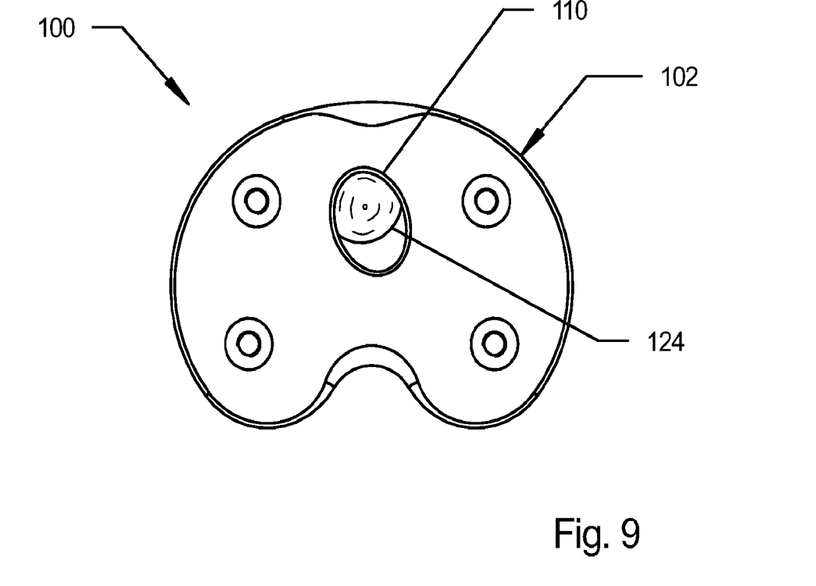
FIG. 9 shows a top plan view of the tibial tray shown in FIGS. 8A and 8B having a plug inserted in an aperture in the tray.

As noted above, the diameter 120 of the aperture 110 shown in FIG. 8A is approximately 12 mm. This size may allow ample room for a surgeon to reattach an ACL during surgery by bringing the ACL or attachment tissue through the aperture 110. Even so, such a relatively large aperture may facilitate an undesirable amount of movement in the ACL during extension and flexion of the knee. To address this issue, the tibial tray system 100 can include a plug 124 such as shown in FIG. 9. The plug 124 can be inserted into the aperture 110 after the ACL is reattached. Such a plug can be configured in any number of ways, such as the plug 124 shown in FIG. 9, which occupies a portion of one side of the aperture 110. Alternatively, such a plug could be made up of a number of shims disposed in a portion of the aperture 110, and even in an annular configuration around the reattached ACL.

Figure 10:
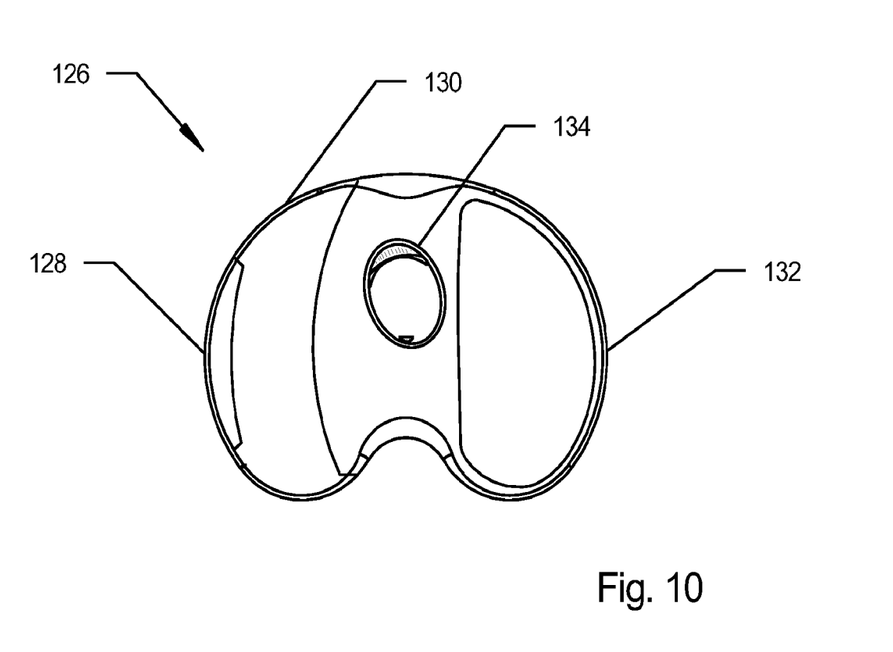
FIG. 10 shows a top plan view of a tibial tray configured for separate tibial inserts in accordance with embodiments of the invention.

FIG. 10 shows a tibial tray 126 in accordance with embodiments of the present invention. The tibial tray 126 is configured similarly to the tibial tray 60 shown in FIG. 4A, in that it is configured to accommodate a movable medial tibial insert and a fixed lateral tibial insert—see, for example, the tibial inserts in FIGS. 5 and 6. A medial side 128 of the tibial tray 126 is configured with an arcuate track 130 that is disposed generally in an A-P direction. The track 130 may be configured as a keyway with a dovetail geometry similar to the track 34 (see FIG. 1). In contrast to the medial side 128 of the tray 126, a lateral side 132 is configured to receive a tibial insert that will be fixed in the tray 126. Such an insert may be secured to the tray 126 via a snap fit or some other known mechanism. The tray 126 also includes an aperture 134 which, like the aperture 110 described in detail above, is configured to allow retention of an ACL through a reattachment procedure.

Two such surgical procedures that can be used in conjunction with ACL retaining tibial tray systems are an allograft procedure and an autograft procedure, which are described below. In an allograft procedure, graft material such as bone-tendon-bone, hamstring complex, Achilles tendon bone or other allograft type replacements can be used. Following the completion of all bone cuts and placement of the femoral implant, the graft is stabilized on the femoral footprint at approximately one o'clock for a left knee and approximately eleven o'clock for a right knee. The graft is then passed through the tibial tray, for example, through the aperture 110 of the tray 112 shown in FIG. 8A. Ensuring that both the medial and lateral tibial insert thicknesses accommodate the distal condylar footprints of the femoral component, and further ensuring the appropriate balancing of the collateral medial and lateral structure, the graft is advanced through the tray aperture, and then through a prepared bone tunnel in the proximal tibia.

The graft can then be fixed to the exterior medial cortex on the tibial side or engaged in some other manner to stabilize the graft to the bony architecture of the tibia. As noted above, balancing the ligament in its position may include using a plug or spacer, including shims, through a portion of the tray aperture. The final position for locking the graft in place occurs in the terminal extended or slightly flexed posture to give the appropriate tension throughout the range of motion and to avoid impingement to the area of the intercondylar notch. The preparation of the tunnels on both the femoral and acetabular side can be in accordance with known techniques for placement of an allograft to both the femoral and tibial side.

In an autograft procedure a guide wire is run from the proximal medial aspect of the tibial cortex, and it is positioned at an approximately 55° angle, which allows the guide wire to enter centrally into the side of the footprint of the ACL. A bone tunnel is prepared of approximately 10-12 mm. Starting from the outer medial cortex, a bone plug is cored to the footprint and base of the ACL ligament. This can be done with a cutting tool which would allow the bone plug to then be freed from its base. The bone is then pushed out of the tunnel from the tibial medial cortex and is extended in an intra-articular manner, elevating it approximately 30 mm, which leaves a high quality bone plug attached to the ACL ligament and allows resection.

The attachment of the ACL to the femur is not disturbed during the autograft procedure, and the graft is positioned at all times into the side of the knee and protected through the phase and preparation for reconstruction using a total knee arthroplasty technique. The femoral component preparation is completed first, followed by the tibial preparation with the full upper tibia resection at 90° along the axis cut with a posterior natural slope and the appropriate dimension resection. Once the upper tibia is free of the proximal tibial bone structure and footprint, prepared tibial trials are used and the routine balancing of the articulation between the femur and tibia can proceed. Appropriate balancing should include the medial and lateral collateral ligaments and the posterior cruciate ligament. Finally, the balancing and positioning of the ACL will take place.

The appropriate position, motion and clearance of the ACL should be ensured. The tibial and femoral components, and the tibial inserts are subsequently applied, and the final placement of the native ACL autograft is then advanced with a guide technique through the tray aperture, overlapping the prior ACL graft harvesting site. This is then advanced down through the anterior cortex medial side of the tibia and brought about using the appropriate technique of fixation to the bone in the area of the tibial bony structures. The fixation allows a bone-to-bone healing with no tethering effect to the area of the tibial tray. The final fixation technique is dependent upon having anatomical posture maintained for the posterior cruciate ligament, and avoiding any impingement to the femoral component or to the roof of the femoral intercondylar space at terminal extension. Tensioning is used to achieve an isometric orientation of the graft, allowing freedom of flexion and extension with normal tension throughout its range of motion. This is to allow reduplication of the mechanical flexion/extension with the appropriate rolling and sliding with retaining four-bar ligament complex mechanism.

The components described in the tibial tray system 10, and the components of other embodiments of the present invention, may be made from any material having the engineering properties and physiologic compatibility desired for such an implant. For example, various metals, such as cobalt chrome and titanium alloys, can be used. One or more of the surfaces of these metal components can be porous coated or covered with hydroxyapatite, or other materials known to facilitate bone growth. Ceramic materials may also be used, as well as polymeric materials, particularly for a tibial insert system. It should also be noted that as used herein, a "sagittal" plane need not bisect the body into two equal halves; rather, it refers to a plane cuts anywhere through the body in an anterior-posterior direction. Therefore sections viewed in a sagittal plane are viewed in a medial-lateral direction. Similarly, as used herein, a "coronal" plane need not bisect the body into two equal halves; rather, it refers to a plane cuts anywhere through the body in a medial-lateral direction. Therefore sections viewed in a coronal plane are viewed in an anterior-posterior direction.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A tibial tray system for a knee, comprising:
   a tibial tray configured for attachment to a surgically-prepared surface of a proximal end of a tibia, the tibial tray including a tapered hole therein; and
   a plurality of splines, each having a respective distal side and tapered shank extending outward therefrom at a different predetermined anterior-posterior (A-P) position, each of the tapered shanks being configured to securely engage the tapered hole in the tibial tray, each of the splines extending proximally from the tibial tray when engaged with the tapered hole and including a posteriorly oriented bearing surface having a projection sized and positioned such that the projection extends farther in a posterior direction on a distal portion of the bearing surface than on a proximal portion of the bearing surface and farther in a posterior direction on a lateral side of the bearing surface than on a medial side of the bearing surface.

2. The tibial tray system of claim 1, further comprising a tibial insert system including a lateral tibial insert and a medial tibial insert, one of the lateral tibial insert or the medial tibial insert being a movable tibial insert configured to move in a generally A-P direction relative to the tibial tray and the other of the lateral tibial insert or the medial tibial insert being a fixed tibial insert configured for fixed attachment to the tibial tray.

3. The tibial tray system of claim 2, wherein the tibial tray includes an arcuate track disposed in a generally A-P direction and configured to cooperate with the movable tibial insert to facilitate movement of the movable tibial insert along the track.

4. The tibial tray system of claim 2, wherein the fixed tibial insert includes a generally arcuate articular surface.

5. The tibial tray system of claim 1, wherein each of the splines includes a reduced edge along a respective proximal anterior portion thereof.

6. The tibial tray system of claim 1, wherein the tibial tray further includes a platform and a keel extending outward from the platform.

7. A tibial tray system for a knee, comprising:
   a tibial tray configured for attachment to a surgically-prepared surface of a proximal end of a tibia, the tibial tray including a platform having an attachment feature; and
   a spline extending proximally from the tibial tray and configured to mate with the attachment feature to secure the spline to the attachment feature in a predetermined position, the spline including a posteriorly oriented bearing surface configured to contact a femoral component of a knee prosthesis such that the femoral component slidingly engages the bearing surface from a proximal position on the bearing surface to a distal position on the bearing surface as the knee moves from an extension position to a flexion position, the bearing surface including a distal lateral eminence sized and positioned such that the eminence extends farther in a posterior direction on a distal portion of the bearing surface than on a proximal portion of the bearing surface, and farther in a posterior direction on a lateral side of the bearing surface than on a medial side of the bearing surface.

8. The tibial tray system of claim 7, wherein the attachment feature comprises a tapered hole and the tibial tray is configured with a tapered shank to mate with the tapered hole, and wherein the tapered shank is disposed at a predetermined anterior-posterior (A-P) position along a distal side of the spline.

9. The tibial tray system of claim 8, further comprising a plurality of the splines, each having a respective tapered shank extending outward from a respective distal side at a different predetermined A-P position.

10. The tibial tray system of claim 7, further comprising a tibial insert system including a lateral tibial insert and a medial tibial insert, one of the lateral tibial insert or the medial tibial insert being a movable tibial insert configured to move in a generally A-P direction relative to the tibial tray and the other of the lateral tibial insert or the medial tibial insert being a fixed tibial insert configured for fixed attachment to the tibial tray.

11. The tibial tray system of claim 10, wherein the tibial tray includes an arcuate track disposed in a generally A-P direction and configured to cooperate with the movable tibial insert to facilitate movement of the movable tibial insert along the track, the track being offset from an A-P axis.

12. The tibial tray system of claim 11, wherein the fixed tibial insert includes a generally arcuate articular surface offset from an A-P axis.

13. The tibial tray system of claim 12, wherein the offset for at least one of the track and the articular surface of the fixed tibial insert is chosen based on radiographic information specific to a particular patient.

14. The tibial tray system of claim 7, wherein the attachment feature comprises a track disposed in a generally anterior-posterior (A-P) direction, and the tibial tray is configured with a tracking feature sized and shaped to fit at least partially within the track.

15. The tibial tray system of claim 7, wherein the tibial tray further includes a keel extending outward from the platform.

16. A tibial tray system for a knee, comprising:
   a plurality of splines, each of the splines including a respective shank having a taper, each of the shanks extending from a distal surface of a respective spline at a different anterior-posterior (A-P) position, and wherein each of the splines includes a bearing surface having a distal lateral eminence sized and positioned such that the eminence extends farther in a posterior direction on a distal portion of the bearing surface than on a proximal portion of the bearing surface, and farther in a posterior direction on a lateral side of the bearing surface than on a medial side of the bearing surface; and
   a tibial tray configured for attachment to a surgically-prepared surface of a proximal end of a tibia, the tibial tray including a single receiving hole through a proximal surface thereof, the receiving hole being tapered and sized and shaped to receive and securely mate with the tapers of the shanks.

17. The tibial tray system of claim 16, further comprising at least one screw hole disposed therethrough and configured for receiving a screw to secure the tibial tray to a patient's tibia.

18. The tibial tray system of claim 16, further comprising a tibial insert system including a lateral tibial insert and a medial tibial insert, one of the lateral tibial insert or the medial tibial insert being a movable tibial insert configured to move in a generally A-P direction relative to the tibial tray and the other of the lateral tibial insert or the medial tibial insert being a fixed tibial insert configured for fixed attachment to the tibial tray.

19. The tibial tray system of claim 18, wherein the tibial tray includes an arcuate track disposed in a generally A-P direction and configured to cooperate with the movable tibial insert to facilitate movement of the movable tibial insert along the track.

20. The tibial tray system of claim 18, wherein the fixed tibial insert includes a generally arcuate articular surface.

* * * * *